(12) United States Patent
Maslowski et al.

(10) Patent No.: US 12,208,283 B2
(45) Date of Patent: Jan. 28, 2025

(54) DRIVING DETERMINISTIC DOSE DEPOSITIONS WITH MONTE CARLO SOURCE MODELING

(71) Applicant: Siemens Healthineers International AG, Steinhausen (CH)

(72) Inventors: Alexander Maslowski, Peachtree City, GA (US); Douglas Allen Barnett, Palo Alto, CA (US); Todd Wareing, Palo Alto, CA (US)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 330 days.

(21) Appl. No.: 17/692,082

(22) Filed: Mar. 10, 2022

(65) Prior Publication Data

US 2023/0285773 A1 Sep. 14, 2023

(51) Int. Cl.
*A61N 5/10* (2006.01)
(52) U.S. Cl.
CPC ............. *A61N 5/1031* (2013.01); *A61N 5/10* (2013.01); *A61N 2005/1034* (2013.01); *A61N 2005/1087* (2013.01); *A61N 2005/1089* (2013.01)
(58) Field of Classification Search
None
See application file for complete search history.

(56) References Cited

U.S. PATENT DOCUMENTS

2006/0285640 A1* 12/2006 Nizin ................... G06F 30/00
378/65

OTHER PUBLICATIONS

International Search Report and Written Opinion on PCT App. PCT/US2023/013938 dated Jun. 16, 2023 (12 pages).
Padilla-Cabal Fatima et al: "Implementation of a dose calculation algorithm based on Monte Carlo simulations for treatment planning towardsMRI guided ion beam therapy", Physica Medica, Acta Medica Edizioni E Congress!, Rome, It, vol. 74, May 29, 2020 (May 29, 2020), pp. 155-165, XP086157026, ISSN: 1120-1797, DOI: 10.1016/J.EJMP.2020.04.027 [retrieved on May 29, 2020].
Padilla-Cabal, Fatima et al: "Benchmarking a GATE/Geant4 Monte Carlo model for proton beams in magnetic fields", Med. Phys.,vol. 47, No. 1, Jan. 1, 2020 (Jan. 1, 2020), pp. 223-233, XP93051386, ISSN: 0094-2405, DOI: https://doi.org/10.1002/mp.13883.
Failla, Gregory et al. "XB advanced dose calculation for the Eclipse TM treatment planning system." Varian Medical Systems, Clinical Perspectives (2010).
Tillikainen L. et al.: "Determination of parameters for a multiple-source model of megavoltage photon beams using optimization methods", Physics in Medicine and Biology, Mar. 7, 2007; 52(5):1441-67. doi: 10.1088/0031-9155/52/5/015.

(Continued)

*Primary Examiner* — Edwin C Gunberg
(74) *Attorney, Agent, or Firm* — Foley & Lardner LLP

(57) ABSTRACT

Embodiments described herein provide for coupling Monte Carlo source modeling with deterministic dose calculations. An internal volumetric first scatter distributed source of a patient is determined using Monte Carlo simulations and ingested into one or more dosing algorithms. The dosing algorithms use the source model to determine a dose deposition.

20 Claims, 6 Drawing Sheets

(56) References Cited

OTHER PUBLICATIONS

Torsti, T. et al. "Using Varian Photon Beam Source Model for Dose Calculation of Small Fields." Dated: Oct. 19, 2012. Whitepaper, Varian Medical Systems.
International Preliminary Report on Patentability and Written Opinion on International Application No. PCT/US2023/013938 dated Sep. 10, 2024 (5 pages).

* cited by examiner

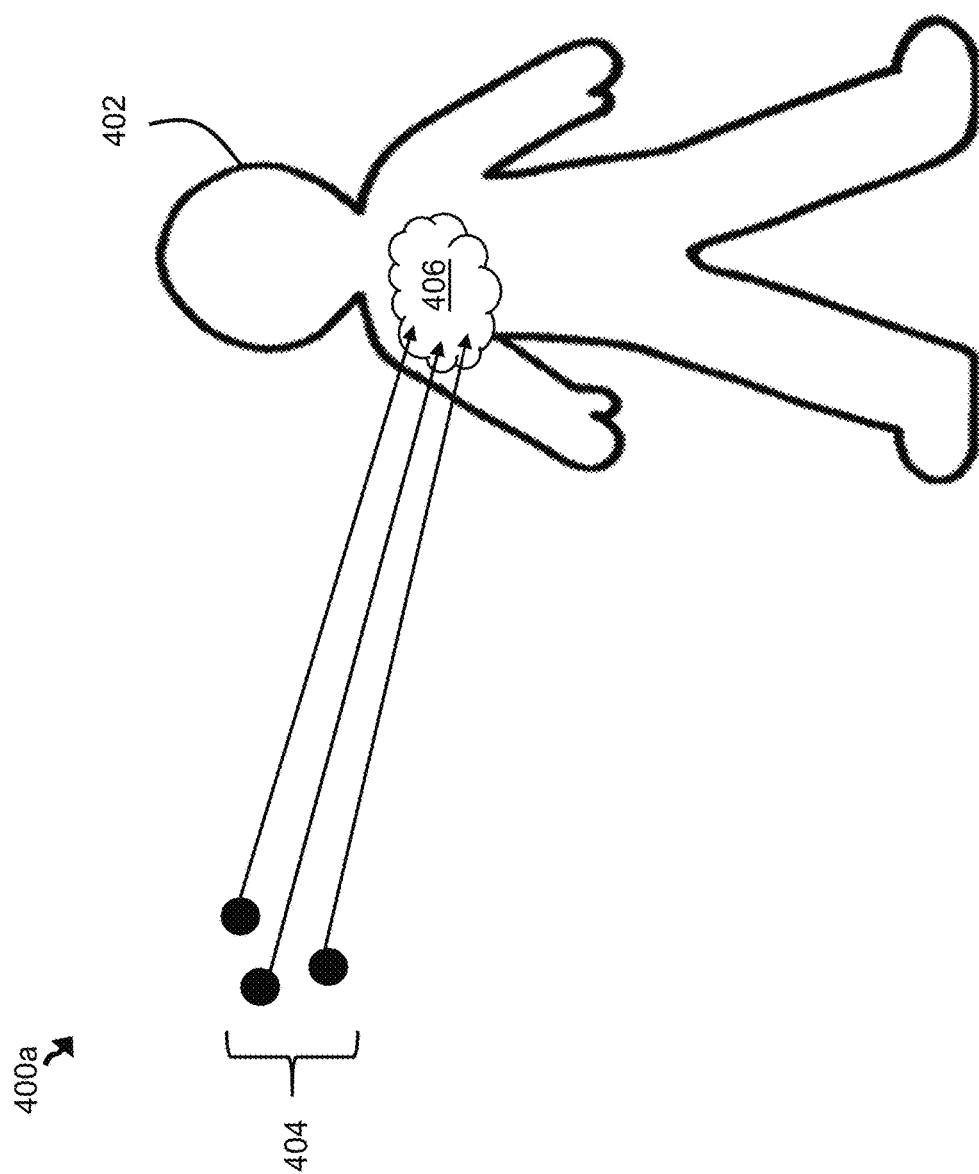

DRIVING DETERMINISTIC DOSE DEPOSITIONS WITH MONTE CARLO SOURCE MODELING

TECHNICAL FIELD

This application relates generally to modeling dose deposition for radiotherapy treatment.

BACKGROUND

Radiation therapy is a localized treatment using ionizing radiation for a specific target tissue, such as a cancerous tumor. Ideally, radiation therapy is performed on target tissue (also referred to as the planning target volume) that spares the surrounding normal tissue from receiving doses above specified tolerances, thereby minimizing the risk of secondary toxicities from damage to healthy tissue. Due to the strong biological impact of the ionizing radiation emitted from a radiation therapy machine, it is imperative that treatment directives are precisely calculated and followed. Treatment directives (also referred to as treatment attributes) may refer to various directives of how a patient's treatment is implemented, including attributes of a radiation therapy machine while the patient is receiving the prescribed radiotherapy dose and how the dosage is delivered to the patient's organs. For instance, the prescribing physician may identify a source location (e.g., patient's organ to be treated or tumor to be eradicated) and a corresponding dosage. These treatment directives may be stored as part of a radiation therapy treatment plan (RTTP).

Various radiotherapy treatments (e.g., very high energy electrons, magnetic resonance linear accelerators, traditional electron treatments, small target for photon treatments, cone treatments, etc.) have complex beam geometries. Generally, determining how the dosage is delivered to the patient's tissue can be sub-divided into at least two tasks: (1) modeling the radiation produced by a linear accelerator providing the radiation therapy (e.g., source modeling), and (2) calculating/modeling the dosage received by the patient (e.g., the dose deposition). The simulated behavior of the radiation (source model) is imported into its downstream models to calculate the dose received by the patient. Inaccuracies in the source modeling may propagate to inaccuracies in the dosage calculations.

In some conventional implementations, nondeterministic probabilistic methods such as Monte Carlo (MC) simulations can simulate how radiation behaves. MC simulations statistically estimate multiple possible outcomes of particular events (e.g., particle location, energy, direction, etc.) by simulating random repeated sampling of each particle. In other implementations, finite element methods, finite volume methods, and other deterministic methods may be performed to simulate how radiation behaves. Nondeterministic methods and deterministic methods may trade speed and accuracy. For instance, MC simulations may achieve higher accuracy simulations of radiation behavior than deterministic methods because convergence for MC depends on a number of particle-histories simulated, not on mesh refinement (or the number of features) in a computed tomography image. The simulation of many events for many particles implies that MC simulations are too slow for clinical applications, although these solutions are accurate because they do not depend on features of an image. In contrast, deterministic methods may converge to a radiation behavior solution faster than MC simulations by simulating the behavior of the entire statistical populations of particles and events. Accordingly, deterministic methods consume less computational power and have a reduced run-time, but may be less accurate and require more memory.

Improvements in imaging technology may result in the detection of cancerous tumors at early stages in the tumor development. As such, the size of the tumor may be small (e.g., less than 5-10 mm), necessitating accurate and targeted radiation at that tumor to minimize damage to healthy tissue. Without accurate dose predictions, it is difficult to create an optimal treatment plan for the patient (e.g., minimizing damage to healthy tissue while shrinking the size of the cancerous tumor), verify the treatment plan (e.g., calculate final dose calculations), and validate the treatment plan.

In the context of such small tumors, empirical models are underperforming, due, in part, to the generality of such models. For example, empirical models, such as the analytical anisotropic algorithm (AAA), model the source by modeling contributions of primary radiation and secondary radiation to the model. Primary radiation may be described as the radiation originating from the source of the accelerator without touching any of the walls of the accelerator. Secondary radiation (including secondary photons and electrons) may be described as the radiation that results from a scattering of the photons and electrons from within the accelerator and arriving at the patient. Conventionally, secondary radiation measurements have been determined using measurements of radiation in water.

Empirical models may be used to determine particle scattering, as shown in FIG. 1. As shown, a beam may be projected from an accelerator onto a surface. The beam has an axis 160 (e.g., a line between the beam's focal point and the isocenter 164). The beam has field size 162 resulting from primary radiation that diverges from the focal point. The inner region of the beam (indicated between upper bound 166-1 and a lower bound 166-2) is the region in which both primary radiation and scatter radiation overlap. A penumbra and outer region outside of upper bound 166-1 and lower bound 166-2 are regions where the scatter radiation is the sole contributor to the tissue's dose.

The fluence and spectrum of the beam may be mapped into a grid between the upper bound 166-1 and the lower bound 166-2. Measurements of the beam may be used to determine the strength of primary radiation exiting fluence window of the accelerator. Accordingly, particle information is determined using empirical relationships. For example, measurements of the beam at various positions between the upper bound 166-1 and the lower bound 166-2 may be extrapolated to determine the direction and energy of particles of the beam. Therefore, an approximated radiation behavior is determined based on measured information. However, it has been observed that as beams target smaller tumors, accuracy also decreases. The decrease in accuracy may be attributed to overly broad assumptions of electron contamination. Generally, precomputed quantities (such as those used to model radiation behavior in dose spread kernel algorithms) and generalized assumptions should be avoided when calculating dosages received by patients.

SUMMARY

There is a desire for a model that can accurately model an advanced beam/linear accelerator geometry in dose depositions that can be flexibly applied to various models (or types) of linear accelerator machines and performed in a short calculation run-time. Moreover, it is desired that the model output simulated data to dosage calculation methods/dosing algorithms, including a deterministic dosage calculation technique. In this manner, subsequent dosing algorithms directly ingest non-empirical, non-deterministic particle behavior, improving the accuracy of the modeled radiation behavior and the dosage calculation. Embodiments disclosed herein use a dosing algorithm that receives an output from the MC simulation for source modeling. By coupling MC analyses to fast dosing algorithms, the accuracy of the fast dosing algorithm may be improved with little impact on its run-time. Moreover, the computational efficiency of a system may be improved as resources can be diverted to performing other operations in response to the smaller dosage-calculation run time. Additionally or alternatively, determining an initial accurate source model using MC reduces the need to repeat source model simulations/calculations, improving the availability of processing power.

In one embodiment, a method may comprise executing, by a processor, a model to determine behavior data of each radiation particle of a plurality of radiation particles exiting a radiotherapy machine during radiotherapy treatment of a patient where at least a portion of the plurality of the radiation particles collide with an anatomical region of the patient; and transmitting, by the processor, the behavior data of at least a portion of the plurality of the radiation particles to a second processor, whereby the second processor determines a dose deposition using a dosing algorithm.

Determining the behavior data of each radiation particle of the plurality of radiation particles comprises may employ a nondeterministic particle behavior simulator. The dosing algorithm may receive an output from the nondeterministic particle behavior simulator.

The behavior data of each radiation particle may be determined by estimating an outcome of each particle location, each particle energy, and each particle direction by randomly sampling each radiation particle of the plurality of radiation particles. The behavior data of each radiation particle of the plurality of particles may use three coordinate dimensions, three angular dimensions, and/or one energy dimension.

The dosing algorithm may be used to determine a flux distribution abstracting a particle reaction rate with the anatomical region of the patient.

The method may further comprise aggregating the behavior data of each radiation particle of the plurality of particles into a first distributed scatter source. The first distributed scatter source may be a description of the spatial energy and angular description of a first interaction of the radiation particles colliding with the anatomical region of the patient.

The method may further comprise encoding the behavior data of each radiation particle of the plurality of particles into a source vector.

In another embodiment, a system may comprise a server comprising a first processor, a second processor, and a non-transitory computer-readable medium containing instructions that when executed by the first processor and the second processor causes the first processor and the second processor to perform operations comprising: executing, by the first processor, a model to determine behavior data of each radiation particle of a plurality of radiation particles exiting a radiotherapy machine during radiotherapy treatment of a patient where at least a portion of the plurality of the radiation particles collide with an anatomical region of the patient; and transmitting, by the first processor, the behavior data of at least a portion of the plurality of the radiation particles to the second processor, whereby the second processor determines a dose deposition using a dosing algorithm.

Determining the behavior data of each radiation particle of the plurality of radiation particles may employ a nondeterministic particle behavior simulator. The processors may be configured such that the dosing algorithm receives an output from the nondeterministic particle behavior simulator.

The behavior of each radiation particle may be determined by estimating an outcome of each particle location, each particle energy, and each particle direction by randomly sampling each radiation particle of the plurality of radiation particles. The behavior data of each radiation particle of the plurality of particles may use three coordinate dimensions, three angular dimensions, and/or one energy dimension.

The dosing algorithm may be used to determine a flux distribution abstracting a particle reaction rate with the anatomical region of the patient.

The first processor may be further configured to aggregate the behavior data of each radiation particle of the plurality of particles into a first distributed scatter source. The first distributed scatter source may be a description of the spatial energy and angular description of a first interaction of the radiation particles colliding with the anatomical region of the patient.

The first processor may be further configured to encode the behavior data of each radiation particle of the plurality of particles into a source vector.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

FIG. 4A illustrates a MC simulation of radiation behavior, according to an embodiment.

DETAILED DESCRIPTION

Figure 1:
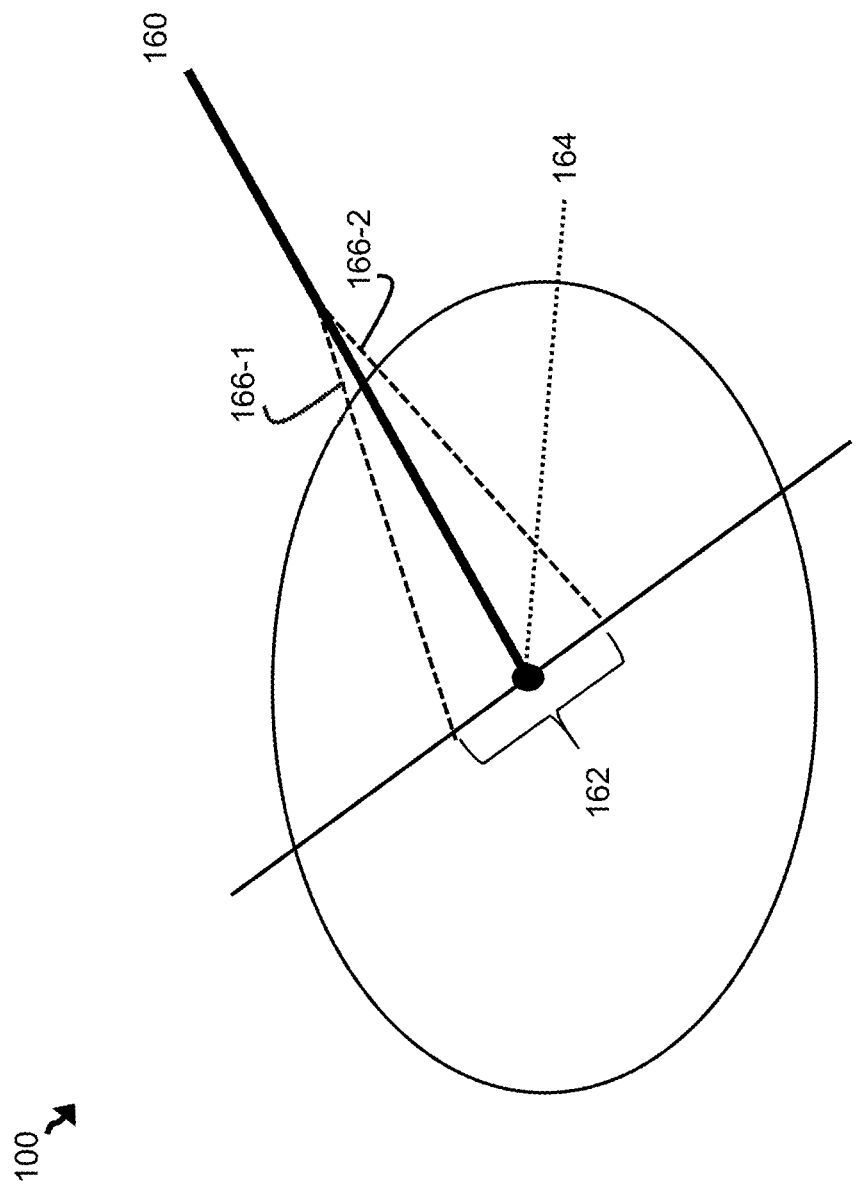
FIG. 1 illustrates a conventional example of using empirical methods to determine particle scattering.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Clinics may utilize software solutions for radiation therapy treatment planning. The software solutions may analyze patient data, clinical guidelines, clinical goals, and a multitude of other factors to generate a customized treatment plan for a patient including an optimal dose deposition that maximizes radiation that targets the cancerous tumor and minimizes radiation affecting healthy tissue. The software solutions may include a set of computer-readable instructions stored on a non-transitory computer medium and configured to be executed by a processor to carry out this functionality.

Figure 2:
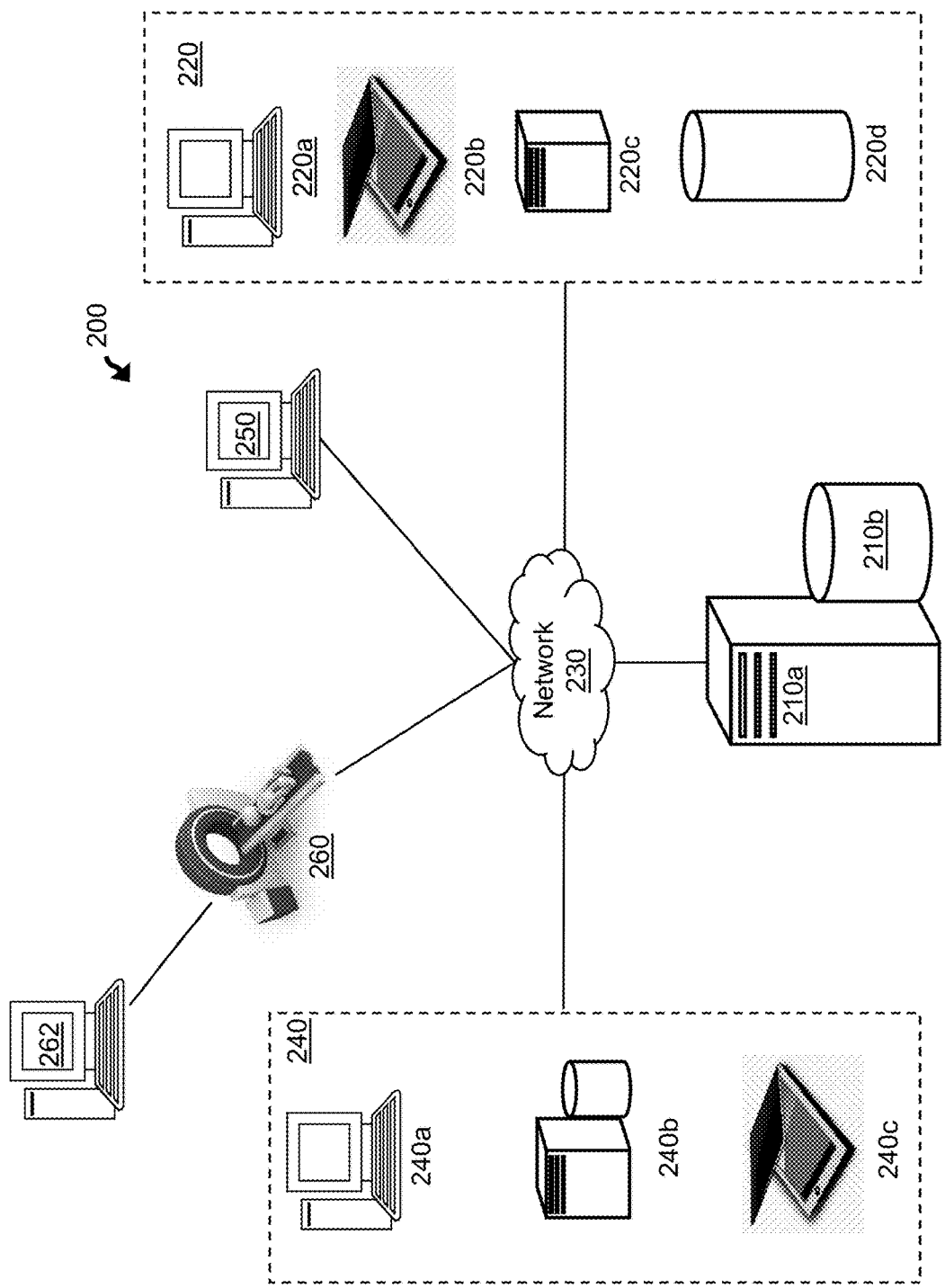
FIG. 2 illustrates components of a system configured to drive deterministic dose simulations using MC source modeling, according to an embodiment.

FIG. 2 illustrates components of a system 200 configured to drive deterministic dose simulations using MC source modeling, according to an embodiment. The system 200 may include an analytics server 210a, system database 210b, electronic data sources 220a-d (collectively electronic data sources 220), end-user devices 240a-c (collectively end-user devices 240), an administrator computing device 250, and a medical device 260 having a medical device computer 262. Various components depicted in FIG. 2 may belong to (e.g., physically located at) a radiotherapy clinic at which patients may receive radiotherapy treatment, in some cases via one or more radiotherapy machines located within the clinic (e.g., medical device 260). The above-mentioned components may be connected to each other through a network 230. Examples of the network 230 may include, but are not limited to, private or public LAN, WLAN, MAN, WAN, and the Internet. The network 230 may include wired and/or wireless communications according to one or more standards and/or via one or more transport mediums.

The communication over the network 230 may be performed in accordance with various communication protocols such as Transmission Control Protocol and Internet Protocol (TCP/IP), User Datagram Protocol (UDP), and IEEE communication protocols. In one example, the network 230 may include wireless communications according to Bluetooth specification sets or another standard or proprietary wireless communication protocol. In another example, the network 230 may also include communications over a cellular network, including, e.g., a GSM (Global System for Mobile Communications), CDMA (Code Division Multiple Access), EDGE (Enhanced Data for Global Evolution) network.

The system 200 is not confined to the components described herein and may include additional or other components, not shown for brevity, which are to be considered within the scope of the embodiments described herein.

The analytics server 210a may execute an electronic platform configured to use various computer models to display RTTP information including a dose deposition. The electronic platform may include one or more graphical user interfaces (GUIs) displayed on each electronic data source 220, the administrator computing device 250, and/or end-user devices 240. An example of the electronic platform generated and hosted by the analytics server 210a may be a web-based application or a website configured to be displayed on different electronic devices, such as mobile devices, tablets, personal computers, and the like. In a non-limiting example, a physician operating the physician device 220b may access the platform, input patient attributes and other data, and further instruct the analytics server 210a to model the source and determine a dose deposition received by the patient.

The operations invoked by the analytics server 210a to determine a dose deposition may be part of the operations in a sequence of operations to optimize a patient treatment plan. That is, the results of the analytics server 210a may be transmitted to other processors or devices to optimize other radiotherapy treatment directives. For example, a first processor of the analytics server 210a may determine a source model and a second processor of the analytics server 210a may determine a dose deposition by ingesting the source model.

The analytics server 210a may display dose depositions used for proton radiation, photon radiation, and electron radiation. The analytics server 210a may display the RTTP information including the calculated dose depositions on an end-user device 240c, medical computing device 262, medical device 260, administrator device 250, and/or a medical professional device 220b. The analytics server 210a may also use the calculated dose depositions in one or more downstream applications. For example, a downstream application may determine information such as radiation parameters including beam angles, side effect prediction, machine therapy attributes such as gantry position, beam blocking devices, treatment frequency, treatment timing, and treatment modalities, among others. Further, the analytics server 210a may transmit the calculated dose depositions to one or more other servers (e.g., clinic server 240b) such that a different device uses the dose deposition in one or more downstream applications. Additionally, or alternatively, the analytics server 210a (or other server) may adjust the configuration of one of the end-user devices 240 (e.g., the end-user device 240c) based on the determined dosages.

The analytics server 210a may host a website accessible to users operating any of the electronic devices described herein (e.g., end-users, medical professionals), where the content presented via the various webpages may be controlled based upon each particular user's role or viewing permissions. The analytics server 210a may be any computing device comprising a processor and non-transitory machine-readable storage capable of executing the various tasks and processes described herein. Non-limiting examples of such computing devices may include workstation computers, laptop computers, server computers, and the like. While the system 200 includes a single analytics server 210a, in some configurations, the analytics server 210a may include any number of computing devices operating in a distributed computing environment, such as a cloud environment.

The analytics server 210a may execute software applications configured to display the electronic platform (e.g., host a website), which may generate and serve various webpages to each electronic data source 220 and/or end-user devices 240. Different users may use the website to view and/or interact with RTTP results, including the determined dose depositions. Servers, such as analytics server 210a, server 220c and/or clinic server 240b, may use the RTTP results in downstream processing (e.g., optimize one or more other radiation parameters and/or treatment plan attributes). The analytics server 210a may also store data associated with each user operating one or more electronic data sources 220 and/or end-user devices 240.

The analytics server 210a may be configured to require user authentication based upon a set of user authorization credentials (e.g., username, password, biometrics, cryptographic certificate, and the like). The analytics server 210a may access the system database 210b configured to store user credentials, which the analytics server 210a may be configured to reference in order to determine whether a set of entered credentials (purportedly authenticating the user) match an appropriate set of credentials that identify and authenticate the user.

The analytics server 210a may generate and host webpages based upon a particular user's role within the system 200. In such implementations, the user's role may be defined by data fields and input fields in user records stored in the system database 210b. The analytics server 210a may authenticate the user and may identify the user's role by executing an access directory protocol (e.g. LDAP). The analytics server 210a may generate webpage content that is customized according to the user's role defined by the user record in the system database 210b.

The analytics server 210a may receive patient data (e.g., medical images, height, weight, diagnosis, age, equipment, etc.) from a user (or retrieves such data from a data repository), analyzes the data, and displays the results on the electronic platform. For instance, in a non-limiting example, the analytics server 210a may query and retrieve RTTP data (including medical images) from the database 220d and execute one or more instructions to model a source of radiation and determine a dose deposition for the patient. The analytics server 210a may then display the results to be interacted with via the electronic platform on the administrator computing device 250, the end-user devices 240, and/or the electronic physician device 220b.

The electronic data sources 220 may represent various electronic data sources that contain, retrieve, and/or input data associated with a patient's treatment plan including patient data and treatment data. For instance, the analytics server 210a may use the clinic computer 220a, medical professional device 220b, the server 220c (associated with a physician and/or clinic), and database 220d (associated with the physician and/or the clinic) to retrieve/receive data associated with a patient's treatment plan.

End-user devices 240 may be any computing device comprising a processor and a non-transitory machine-readable storage medium capable of performing the various tasks and processes described herein. Non-limiting examples of an end-user device 240 may be a workstation computer, laptop computer, tablet computer, and server computer. In operation, various users may use end-user devices 240 to access the GUI operationally managed by the analytics server 210a. Specifically, the end-user devices 240 may include clinic computer 240a, clinic server 240b, and a medical device 240c. Even though referred to herein as "end-user" devices, these devices may not always be operated by end-users. For instance, the clinic server 240b may not be directly used by an end-user. However, the results stored onto the clinic server 240b may be used to populate various GUIs accessed by an end-user via the medical professional device 240c.

The administrator computing device 250 may represent a computing device operated by a system administrator. The administrator computing device 250, along with the medical professional device 240c, physician device 220b, medical computing device 262, and the like, may be configured to display RTTP information such dose depositions determined by the analytics server 210a.

The medical device 260 may be a radiotherapy machine (e.g., a linear accelerator, particle accelerator (including circular accelerators), or a cobalt machine)) configured to implement a patient's radiotherapy treatment. The medical device 260 may emit radiation from a head of an accelerator and may include an imaging device capable of emitting radiation such that the medical device 260 may perform imaging according to various methods to accurately image the internal structure of a patient. For instance, the medical device 260 may include a rotating system (e.g., a static or rotating multi-view system). A non-limiting example of a multi-view system may include a stereo systems (e.g., two systems may be arranged orthogonally). The medical device 260 may also be in communication with a medical computing device 262 that is configured to display various GUIs discussed herein. For instance, the analytics server 210a may display the RTTP information including the dose determined by the analytics server 210a.

In operation, a medical professional may access an application executing on the physician device 220b and input RTTP data (e.g., patient information, patient diagnosis, radiation therapy radiation requirements, and thresholds). The analytics server 210a then uses a patient identifier to query patient data (e.g., patient anatomy and/or medical images) from the electronic data sources 220. The analytics server 210a may also use a radiotherapy machine identifier to query data from the electronic data sources 220 associated with radiotherapy machines (e.g., physical characteristics, dimensions, radiation output). The analytics server 210a may then identify a clinic associated with the patient (e.g., clinic performing the treatment) and retrieve one or more files associated with treatment templates, radiotherapy machine, and clinic rules. The analytics server 210a may then utilize the systems and methods described herein to determine a dose deposition from the patient data and the medical device 260 and display the results onto the physician device 220b, the clinic computer 240a, and/or the medical computing device 262.

The analytics server 210a may be in communication (real-time or near real-time) with the medical computing device 262, end-user device 240 and/or electronic data sources 220, such that a server/computer hosting the medical device 260 can adjust the medical device 260 based on the calculated dose deposition. For instance, the radiotherapy machine may adjust the gantry, beam blocking device (e.g., MLC), and couch based on the dosage calculations. The analytics server 210a may transmit instructions to the radiotherapy machines indicating any number or type of radiation parameters, beam angles, and/or treatment directives to facilitate such adjustments.

As described herein, conventional methods may empirically determine particle location, direction, energy, etc. to model the beam and/or model the source. For example, AAA is an empirical source modeling algorithm. Conventional methods may also execute one or more non-deterministic models to characterize features of a particle (e.g., particle interaction with water) and/or characterize features of a source, where such characterized features are subsequently used with empirical measurements. For example, one or more MC simulations used to assemble a source may be packaged into a model of the source for subsequent use. In these embodiments, while MC simulations may be performed to model the source, the model is applied to particle data in the empirical space. In a particular example, MC simulations may describe the source of an x-ray. However, additional factors (such as beam shaping and error) are determined using empirical measurements.

Figure 3:
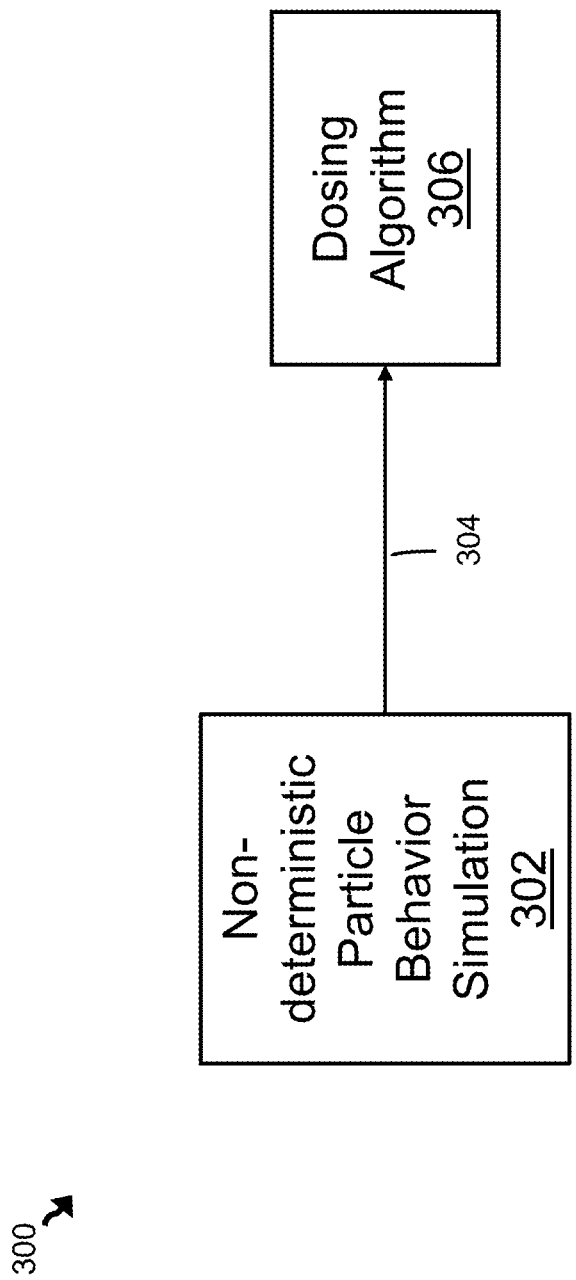
FIG. 3 illustrates a non-limiting visual example of a non-deterministic particle behavior simulation providing an output to a dosing algorithm, according to an embodiment.

Coupling source models to dosing algorithms has traditionally been limited by the input data requirements of the dosing algorithms and/or the output data of the source model. For example, calculating a dosage of modeled radiation behavior of cone treatments is limited by the unique cone treatment data output (e.g., there is no source modeling of cone treatments). FIG. 3 illustrates a non-limiting visual example of outputting from a non-deterministic particle behavior simulation to a dosing algorithm. In this example 300, a high-fidelity MC simulation of radiation behavior (e.g., beam behavior) outputs to a dosing algorithm (e.g., Acuros® dosing algorithm).

In example 300, the analytics server executes a MC particle simulation 302 to generate an internal volumetric first scatter distributed source of the patient to be fed 304 to deterministic dosing algorithm(s) 306 (e.g., Acuros® or Acuros® XB dosing algorithm). Coupling deterministic methods to a MC simulation of radiation provides an estimated fluence from non-scattered (or uncollided) photons and scattered photons and electrons. Accordingly, deterministic methods may be applied beyond photon fields. The fluence from the simulated particles is coupled with deterministic methods to transport the radiation into the patient through all scattering events. The deterministic dosing algorithm(s) 306 continue the particle simulation from the distribution of the first collision to the last collision of the particle with the anatomical region. The deterministic dosing algorithm(s) 306 determine, from this simulation, how particles impart the dose to the patient. Coupling such deterministic methods to the MC simulation increases the accuracy for photon beams larger than 3 cm in size.

Referring to FIG. 4A, illustrated is an example 400a of using a MC simulation executed by an analytics server to determine radiation behavior. As described herein, the MC models photons and electrons exiting one or more accelerators (e.g., a tip of an accelerator or a source) up to a first patient event (e.g., a first interaction with a patient 402 being treated using radiotherapy at a distribution of particles at a first collision site 406). Particle bank 404 represents a description of each particle (e.g., where the particle is, where the particle is traveling to, the direction of the particle, the energy of the particle, etc.) as the particle exits the accelerator. In some embodiments, each particle may be represented in seven dimensions (e.g., three coordinate dimensions, three angular dimensions, and one energy dimension).

The MC simulation is used to sample each particle from their origin in the particle bank 404 to the first collision with the patient's volume at first collision site 406 such that a particle history and interaction of each particle is simulated. Some particles, upon reaching the patient 402 at first collision site 406, may scatter and other particles may be absorbed by the patient 402. The MC simulation is used to sample particles in the particle bank 404 to determine whether the particles are expected to scatter in the patient 402 or be absorbed. If the particles are further scattered, the MC simulation may sample the direction that the particles will travel. Conventionally, MC simulations continue sampling particles to determine an energy, location, next direction traveled by the particles, and a next collision source.

Figure 4B:
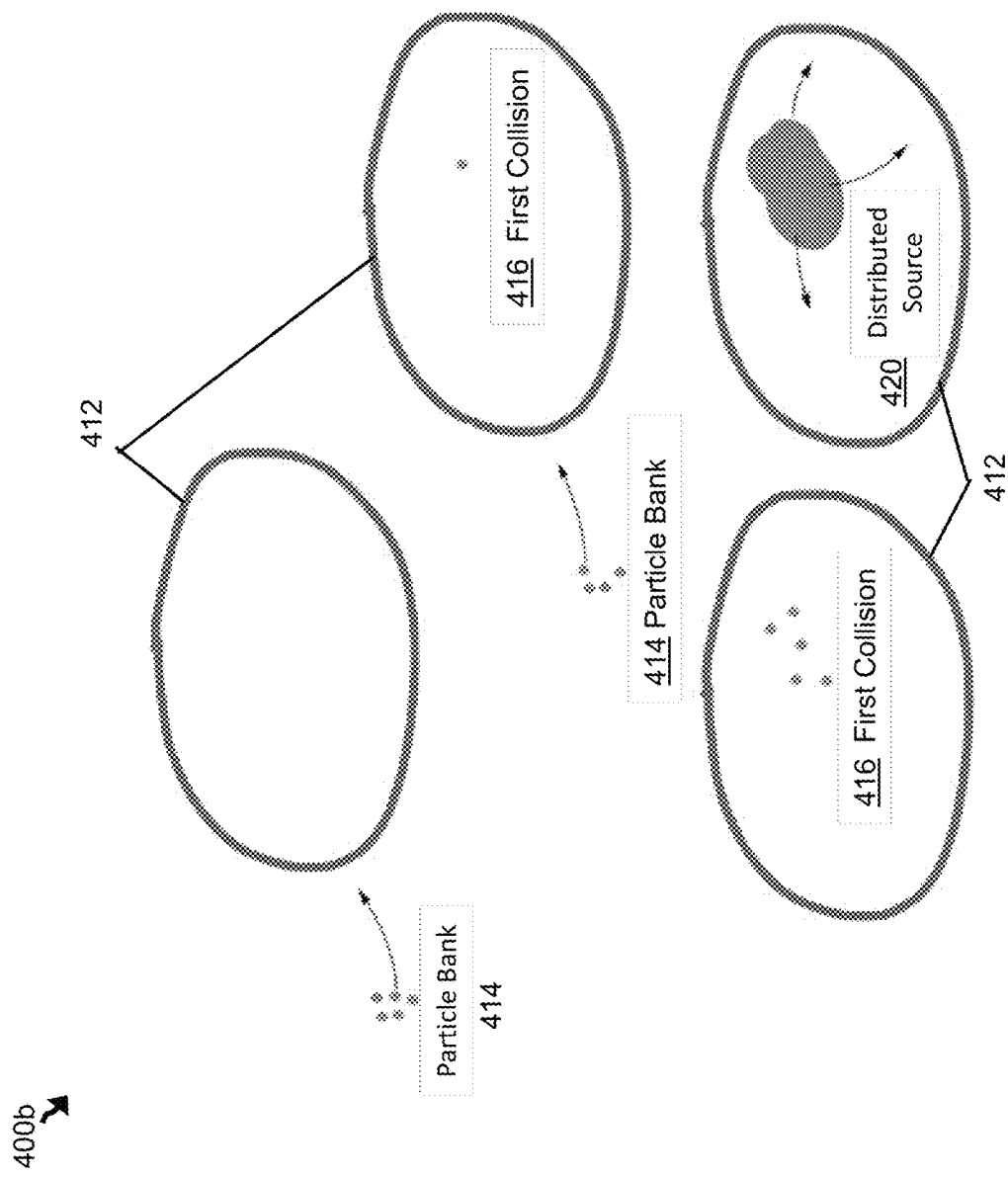
FIG. 4B illustrates a MC simulation of radiation behavior coupled to a deterministic method to determine a dose deposition, according to an embodiment.

FIG. 4B illustrates an alternate example 400b of a MC simulation of radiation behavior coupled to a deterministic method to determine a dose deposition. Particle bank 414 includes a description of each particle exiting one or more accelerators. Particles of the particle bank 414 travel toward a patient 412 being treated using radiotherapy based on a source model (e.g., a MC simulation). As determined using simulation(s), some particles of the particle bank 414 will collide with the patient 412. Other particles of the particle bank 414 may not collide with the patient 412. For example, particles may travel through the patient and not interact with the patient because particles have a stochastic behavior. The particles that collide with the patient are indicated at a first collision event 416. The particles from the particle bank 414 collide with the patient 412 such that the particles are distributed across the patient (e.g., a particular area of the patient). In response to determining a distribution of particles and their first collision events 416, one or more deterministic methods 420 may be used to determine whether the particles are absorbed, how the particles scatter in the patient, how the particles impart their kinetic energy to the patient (e.g., the direction and/or energy of the particles in the patient), and the like.

Referring back to FIG. 3, the analytics server captures the state of the particles after their first interaction with the patient (e.g., the first scatter source at first collision site 406 in FIG. 4A) by accumulating the particles in each voxel as the particles collide with and scatter in the voxel's medium. The analytics server assembles/aggregates the particle data into a first distributed scatter source (sometimes called a beam source). The first distributed scatter source is a description of the spatial energy and angular description of a first interaction of particles with the patient. The analytics server projects the simulated particle data of the first distributed scatter source into finite element space such that the first distributed scatter source can be ingested by dosing algorithms 306. In this manner, the analytics server makes a distribution of the particles at the first scatter distributed source of the patient.

The internal volumetric first scatter distributed source of the patient is ingested by one or more dosing algorithms 306 (e.g., deterministic methods, such as Acuros® or Acuros® XB dosing algorithm, scattering kernels) to calculate a radiation dose received by the patient. For example, the dosing algorithm computes the dose deposited to the patient by solving the Linear Boltzmann Transport Equation (LBTE). The LBTE governs how particles stream through a medium, how particles scatter within the medium, and how particles are absorbed with the medium. Deterministic methods discretize the LBTE into a matrix and iteratively invert the matrix. The solution is a flux distribution (or fluence) that abstracts the particle reaction rate with the medium. The flux is then mapped from the flux to the dose imparted to the medium, and the dose imparted to a water equivalent medium (e.g., dose to material vs dose to medium). Accordingly, the dosing algorithms 306 simulate the particles to at scatter events and compute the dose.

Errors commonly associated with using deterministic methods to solve the LBTE are systematic errors that result from discretizing variables in angle, energy, and/or space. In some embodiments, the analytics server 210a may be configured to improve the convergence speed of deterministic methods (e.g., decrease the run-time) by increasing the step-sizes in the discretization process. However, increasing the step-size results in decreased accuracy.

The analytics server outputs 304 from the non-deterministic particle behavior simulation 302 to dosing algorithms 306, by generating an accurate model of the particles at the first collision site of the patient (e.g., using the MC simulation), encoding the distribution of the particles into a source vector, and employing one or more dosing algorithms to quickly continue scattering the particles in the patient. The result of such a coupled system is a calculated dosage received by the patient.

Figure 5:
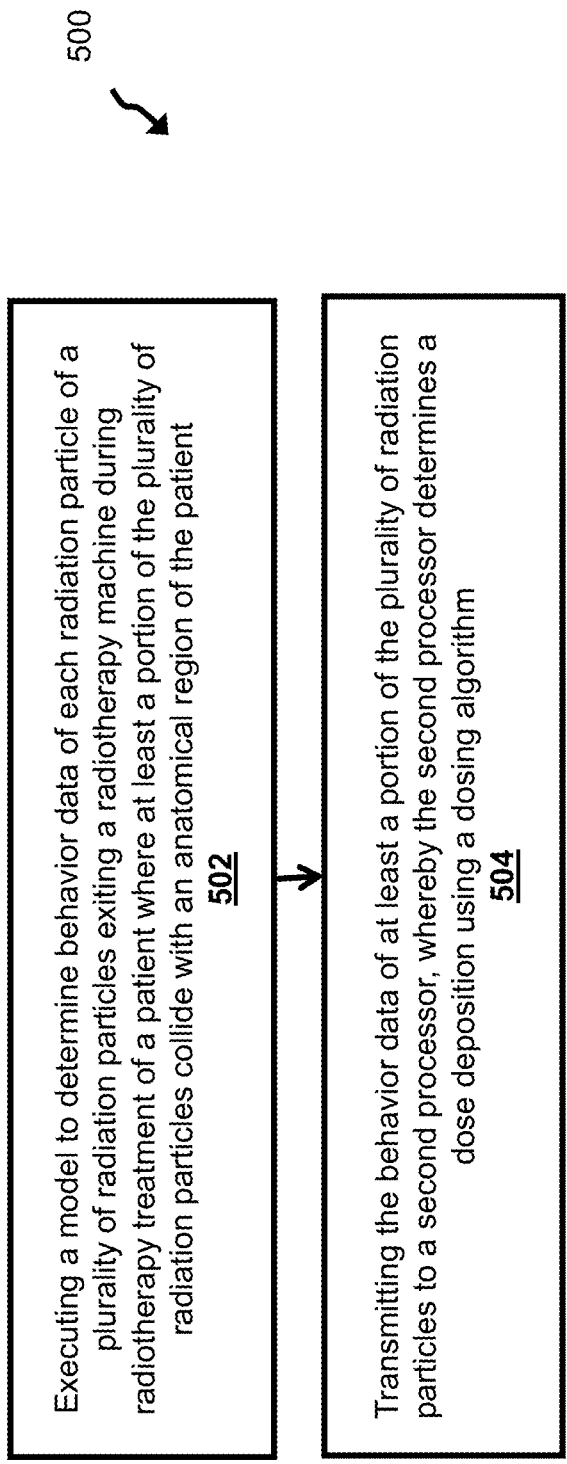
FIG. 5 illustrates a flow diagram of determining dose deposition, according to an embodiment.

As part of the radiotherapy treatment planning, various models may be coupled together to determine a dose deposition of radiation at a particular anatomical region of a patient. FIG. 5 illustrates a flow diagram of determining dose deposition, according to an embodiment. The method 500 may include steps 502-504. However, other embodiments may include additional or alternative steps, or may omit one or more steps altogether.

The method 500 is described as being executed by an analytics server, such as the analytics server described in FIG. 2. The analytics server may employ one or more CPUs and GPUs to perform one or more steps of method 500. The CPUs and/or GPUs may be performed in part by the analytics server and in part by one or more other servers and/or computing devices. The servers and/or computing devices employing the CPUs and GPUs may be local and/or remote (or some combination). For example, one or more virtual machines in a cloud may employ one or more CPUs and GPUs to perform one or more steps of method 500. One or more steps of method 500 may be executed by any number of computing devices operating in the distributed computing system described in FIG. 2. For instance, one or more computing devices may locally perform part or all of the steps described in FIG. 5.

In step 502, the analytics server executes a model to determine behavior data of each radiation particle of a plurality of radiation particles exiting a radiotherapy machine during radiotherapy treatment of a patient. The behavior data of each radiation particle exiting a radiotherapy machine may be characterized as a source model. As described herein, the analytics server simulates photons and electrons exiting one or more accelerators (e.g., a tip of an accelerator, a source) up to a first patient event using a MC simulation. The behavior of each particle may be in seven dimensions (e.g., three coordinate dimensions, three angular dimensions, and one energy dimension).

Some simulated particles may miss the patient being treated for radiotherapy, and other simulated particles may collide with the anatomical region of the patient being treated for radiotherapy. The analytics server aggregates each particle at the first interaction site of the patient. In some implementations, the analytics server aggregates each particle at additional interaction sites of the patient. For example, the analytics server may subsequently sample each of the particles at the first interaction site of the patient to determine a subsequent energy, location, and direction traveled by the particles. The analytics server simulates particles colliding with the patient at an additional (or next) interaction site of the patient in the same anatomical region (or different anatomical regions).

In step 504, the analytics server transmits the behavior of the portion of radiation particles that collided with the anatomical region of the patient at the first collision site to additional processors to determine a dose deposition using a dosing algorithm. In some embodiments, the analytics server transforms the behavior of the radiation particles. For example, the analytics server may encode a probability distribution of each particle into a source vector. The analytics server may perform other operations such as normalizing the source vector, scaling the source vector, and the like. The analytics server feeds the source vector as an input into one or more dosing algorithms. The dosing algorithm(s) may be any dosing algorithm configured to simulate a radiation dose received by the patient. For example, deterministic methods determine how particles stream through a medium, how particles scatter within the medium, and how particles are absorbed in the medium.

In a non-limiting example, a processor executes a MC simulation to determine behavior data of each radiation particle exiting a radiotherapy machine directed at a patient being treated using radiotherapy. The behavior data of each particle may be in seven dimensions (e.g., three coordinate dimensions, three angular dimensions, and one energy dimension). In these embodiments, the direction of the particle (e.g., the angular dimension) may be described by a three-dimensional vector. In some embodiments, the behavior data of each particle may be in six dimensions (e.g., three coordinate dimensions, two angular dimensions, and one energy dimensions). In these embodiments, the direction vector may be normalized to unit length. Accordingly, two dimensions may describe the direction of the particle. The processor assembles/aggregates the behavior data of each particle into an internal volumetric first distributed scatter source. The internal volumetric first distributed scatter source is a description of the spatial energy and angular description of a first interaction of particles with the patient. The processor feeds the internal volumetric first distributed scatter source to one or more deterministic methods to transport the radiation into the patient through all scattering events, generating a dose deposition of the radiation in the patient being treated using radiotherapy. It should be appreciated that determining the dose deposition for a patient being treated using radiotherapy may be performed during radiotherapy treatment of the patient. For example, the dose deposition for the patient may be determined while the patient is present in a radiotherapy clinic (or other office) to receive radiotherapy treatment. Additionally or alternatively, the dose deposition for the patient may be determined during a generation of the radiotherapy treatment plan in preparation of the patient arriving at the radiotherapy clinic (or other office) to receive radiotherapy treatment.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A method comprising:
   executing, by a processor, a model to determine behavior data of each radiation particle of a plurality of radiation particles exiting a radiotherapy machine during radiotherapy treatment of a patient where at least a portion of the plurality of the radiation particles collide with an anatomical region of the patient;
   encoding, by the processor, behavior data of at least a portion of the plurality of radiation particles into a vector; and
   transmitting, by the processor, the vector to a second processor, whereby the second processor determines a dose deposition using a dosing algorithm.

2. The method of claim 1, wherein determining the behavior data of each radiation particle of the plurality of radiation particles comprises employing a nondeterministic particle behavior simulator.

3. The method of claim 2, wherein the dosing algorithm receives an output from the nondeterministic particle behavior simulator.

4. The method of claim 1, wherein the behavior data of each radiation particle is determined by estimating an outcome of each particle location, each particle energy, and each particle direction by randomly sampling each radiation particle of the plurality of radiation particles.

5. The method of claim 1, wherein the behavior data of each radiation particle of the plurality of particles comprises three coordinate dimensions.

6. The method of claim 1, wherein the behavior data of each radiation particle of the plurality of particles comprises three angular dimensions.

7. The method of claim 1, wherein the behavior data of each radiation particle of the plurality of particles comprises an energy dimension.

8. The method of claim 1, further comprising aggregating the behavior data of each radiation particle of the plurality of particles into a first distributed scatter source.

9. The method of claim 8, wherein the first distributed scatter source is a description of the spatial energy and angular description of a first interaction of the radiation particles colliding with the anatomical region of the patient.

10. The method of claim 1, further comprising encoding the behavior data of each radiation particle of the plurality of particles into a source vector.

11. A system comprising:
    a server comprising a first processor, a second processor, and a non-transitory computer-readable medium containing instructions that when executed by the first processor and the second processor causes the first processor and the second processor to perform operations comprising:
    executing, by the first processor, a model to determine behavior data of each radiation particle of a plurality of radiation particles exiting a radiotherapy machine during radiotherapy treatment of a patient where at least a portion of the plurality of the radiation particles collide with an anatomical region of the patient;
    encoding, by the first processor, behavior data of at least a portion of the plurality of radiation particles; and
    transmitting, by the first processor, the vector to the second processor, whereby the second processor determines a dose deposition using a dosing algorithm.

12. The system according to claim 11, wherein determining the behavior data of each radiation particle of the plurality of radiation particles comprises employing a nondeterministic particle behavior simulator.

13. The system according to claim 12, wherein the first processor and second processors are further configured such that the dosing algorithm receives an output from the nondeterministic particle behavior simulator.

14. The system according to claim 11, wherein the behavior data of each radiation particle is determined by estimating an outcome of each particle location, each particle energy, and each particle direction by randomly sampling each radiation particle of the plurality of radiation particles.

15. The system according to claim 11, wherein the behavior data of each radiation particle of the plurality of particles comprises three coordinate dimensions.

16. The method according to claim 11, wherein the behavior data of each radiation particle of the plurality of particles comprises three angular dimensions.

17. The method according to claim 11, wherein the behavior data of each radiation particle of the plurality of particles comprises an energy dimension.

18. The system according to claim 11, wherein the first processor is further configured to aggregate the behavior data of each radiation particle of the plurality of particles into a first distributed scatter source.

19. The system according to claim 18, wherein the first distributed scatter source is a description of the spatial energy and angular description of a first interaction of the radiation particles colliding with the anatomical region of the patient.

20. The system according to claim 11, wherein the first processor is further configured to encode the behavior data of each radiation particle of the plurality of particles into a source vector.

* * * * *